United States Patent [19]

Cole et al.

[11] Patent Number: 4,859,612
[45] Date of Patent: Aug. 22, 1989

[54] METAL SOL CAPTURE IMMUNOASSAY PROCEDURE, KIT FOR USE THEREWITH AND CAPTURED METAL CONTAINING COMPOSITE

[75] Inventors: Francis X. Cole, Stow; Gene Davis, Lexington; Eric Sigillo, Meuthen, all of Mass.

[73] Assignee: Hygeia Sciences, Inc., Newton, Mass.

[21] Appl. No.: 105,285

[22] Filed: Oct. 7, 1987

[51] Int. Cl.$^4$ ................. G01N 33/543; G01N 33/553
[52] U.S. Cl. ..................................... 436/523; 436/525; 436/526; 436/527; 436/531; 436/532; 436/533; 436/534; 436/818; 436/819; 436/824
[58] Field of Search ............... 436/525, 533, 532, 526, 436/527, 531, 534, 523, 818, 819, 824

[56] References Cited

U.S. PATENT DOCUMENTS

| | | | |
|---|---|---|---|
| 3,088,875 | 5/1963 | Fisk | 167/84.5 |
| 3,096,250 | 7/1963 | Ingraham | 167/84.5 |
| 3,652,761 | 3/1972 | Weetall | 424/12 |
| 3,826,613 | 7/1974 | Parikh et al. | 23/230 |
| 3,960,491 | 6/1976 | Giaever | 23/230 |
| 3,970,518 | 7/1976 | Giaever | 195/1.5 |
| 4,018,886 | 4/1977 | Giaever | 424/12 |
| 4,070,246 | 1/1978 | Kennedy et al. | 195/99 |
| 4,092,116 | 5/1978 | Giaever | 23/230 |
| 4,115,535 | 9/1978 | Giaever | 424/1 |
| 4,118,192 | 10/1978 | Sawai et al. | 424/12 |
| 4,157,323 | 6/1979 | Yen | 436/526 X |
| 4,169,138 | 9/1979 | Jonsson | 424/12 |
| 4,184,849 | 1/1980 | Cambiaso et al. | 23/230 |
| 4,203,724 | 5/1980 | Sawai et al. | 23/230 |
| 4,205,952 | 6/1980 | Cais | 23/230 |
| 4,208,185 | 6/1980 | Sawai et al. | 23/230 |
| 4,230,664 | 10/1980 | Cais | 422/61 |
| 4,233,402 | 11/1980 | Maggio et al. | 435/7 |
| 4,241,176 | 12/1980 | Avrameas et al. | 435/7 |
| 4,246,339 | 1/1981 | Cole et al. | 435/7 |
| 4,279,617 | 7/1981 | Masson et al. | 23/230 |
| 4,308,026 | 12/1981 | Mochida et al. | 23/230 |
| 4,313,734 | 2/1982 | Leuvering | 23/230 |
| 4,376,110 | 3/1983 | David et al. | 436/513 |
| 4,397,959 | 8/1983 | Hechemy | 436/509 |
| 4,407,943 | 10/1983 | Cole et al. | 435/7 |
| 4,446,238 | 5/1984 | De Mey et al. | 436/527 |
| 4,459,361 | 7/1984 | Gefter | 436/533 X |
| 4,468,470 | 8/1984 | Aalberse | 436/539 |
| 4,486,530 | 12/1984 | David et al. | 435/7 |
| 4,552,839 | 11/1985 | Gould et al. | 435/7 |
| 4,582,810 | 4/1986 | Rosenstein | 436/533 X |
| 4,595,661 | 6/1986 | Cragle et al. | 436/534 |
| 4,623,901 | 12/1986 | Valkirs et al. | 435/5 |
| 4,628,037 | 12/1986 | Chagnon et al. | 436/526 |
| 4,632,461 | 11/1986 | Hossom et al. | 210/445 |
| 4,636,479 | 1/1987 | Martin et al. | 436/533 |
| 4,727,019 | 2/1988 | Valkirs et al. | 435/5 |

FOREIGN PATENT DOCUMENTS

| | | | |
|---|---|---|---|
| 0045103 | 2/1982 | European Pat. Off. | 436/533 |
| 85/0087 | 12/1985 | PCT Int'l Appl. | |
| 85/02534 | 7/1986 | PCT Int'l Appl. | |

OTHER PUBLICATIONS

Marc Horisberger and Jacqueline Rosset, "Colloidal Gold, a Useful Marker for Transmission and Scanning Electron Microscopy", *J. Histochem. Cytochem.*, vol. 25, 1977, pp. 295–305.
P. K. Chun and A. E. Chu, "Colloidal Gold in Immunodot and Immunofiltration Blot Assays for Rapid Serodiagnosis and Direct Specimen Testing", *Abstracts of the Annual Meeting–1986, International Congress of Immunology*, p. 363, (Abstract C-213).
M. Horisberger, Jacqueline Rosset and H. Bauer, "Colloidal Gold Granules as Markers for Cell Surface Receptors in the Scanning Electron Microscope", *Experimentia*, vol. 31, pp. 1147–1149, Oct. 15, 1975.
Malcolm L. Gefter, David H. Margulies and Matthew D. Scharff, "A Simple Method for Polyethylene Glycol–Promoted Hybridization of Mouse Myeloma Cells", *Somatic Cell Genetics*, vol. 3, No. 2, 1977, pp. 231–236.
Marc J. Shulman and Georges Köhler, "Immunoglobulin $\mu$ and Heavy Chain Classes are not Determined by Class-Specific RNA–Splicing Enzymes", *Nature*, vol. 274, pp. 917–919, (1978).
N. R. Klinman, A. R. Pickard, N. H. Sigal, P. J. Gearhart, E. S. Metcalf and S. K. Pierce, "Assessing B Cell Diversification by Antigen Receptor and Precursor Cell Analysis", *Ann. Immuno. (Inst. Pasteur)*, vol. 127 C, pp. 489–502, (1976).
S. L. Goodman, G. M. Hodges, L. K. Trejdosiewicz and D. C. Livingston, "Colloidal Gold Markers and Probes for Routine Application in Microscopy", *Journal of Microscopy*, vol. 123, Pt. 2, Aug. 1981, pp. 201–213.
G. Frens, "Controlled Nucleation for the Regulation of the Particle Size in Monodisperse Gold Suspensions", *Nature*, 241, pp. 20–22, (1973).

Primary Examiner—Christine M. Nucker
Attorney, Agent, or Firm—Staas & Halsey

[57] ABSTRACT

Antibody coated gold sol particles and antibody coated solid phase particles dispersed in an aqueous system react immunologically as a function of the presence of an analyte in a sample to be analyzed to produce a collectible, solid phase, gold-containing composite. The composite is collected on a filter or at the bottom of a test tube by centrifugation or gravitation and the analyte in the sample is determined or detected by direct visual examination of the collected solid phase composite which has a pink or red or purplish coloration as a result of the gold contained thereby. The materials required for conducting the assay comprise coated gold particles, coated solid phase particles and a collector element such as a filter. The collected, solid phase, metal-containing composite, which may be directly visually examined to determine or detect the gold therein and thus the analyte in the sample, is stable and remains available for confirmation of test results at a later time.

41 Claims, No Drawings

METAL SOL CAPTURE IMMUNOASSAY PROCEDURE, KIT FOR USE THEREWITH AND CAPTURED METAL CONTAINING COMPOSITE

BACKGROUND OF THE INVENTION

1. Field of the Invention

The present invention relates to a process for the determination and detection of an immunologically reactive analyte such as a ligand or ligand receptor in an aqueous sample. More particularly, the invention involves the use of specific binding pairs consisting of immunologically reactive ligands and anti-ligands or ligand receptors which are specifically immunologically reactive, that is bindable, therewith. The invention further relates to kits of materials for use in conducting the process of the invention and to visually determinable or detectable, collected, solid phase, metal-containing composites which are produced in accordance with the procedure.

2. Description of the Prior Art

There has long been a need to measure substances with a high degree of sensitivity and specificity. In particular, in fields such as clinical medicine, forensic science, environmental quality testing, food quality assurance, drug testing and other related areas, the presence and/or amount of trace substances in test samples is often of great significance. In such areas, the measurement of very low concentrations in the order of parts per million or less is sometimes necessary. Moreover, such testing or measurement often requires the identification of particular molecules while not sensing other molecules with similar yet different structures.

The need for sensitive and specific tests has been addressed in the past by the development of a number of immunoassay procedures based on the highly specific and sensitive interaction between an antigen and an antibody directed against such antigen Antigens and antibodies were initially recognized as being the participants in the immune process of an animal, that is, when an animal is injected with a foreign substance that is an antigen (or ANTIbody GENerator), the animal in time responds by producing antibodies which are protein molecules that recognize and tightly bind the invading antigen thereby facilitating removal or destruction of the latter. The immune process is highly specific and the use of immunoassay procedures for identification of specific substances has been exploited with great success. Such procedures have been further facilitated by the important discovery of Milstein and Kohler reported in Nature 256:495–497, 1975, concerning a procedure for preparing so-called monoclonal antibodies The details of this work are well known and there is no need to repeat the same here; however, as a result of the Milstein and Kohler work, the development of highly sensitive and specific reagents has been facilitated.

In the known prior assay procedures referred to as radioimmunoassay (RIA) procedures, either an antibody or an antigen is labelled with a radioisotope such as $I^{125}$. In accordance with these known procedures, the amount of the radioisotope in an immune complex may be measured and is a function of the presence or quantity of analyte in the test solution. As is well known in the art, radioimmunoassays may be configured in a variety of ways employing competitive or immune sandwich formats, to name but a few. RIA procedures have been configured for detection of both large analytes such as macromolecules and much smaller substances comprising small molecules such as theophylline. At the present time, any substance which is antigenic or which may be rendered antigenic by coupling to a suitable carrier can be detected by a RIA procedures, and such procedures have been found widespread acceptance, especially in clinical diagnostic laboratories, as a result of the high degree of sensitivity and specificity which can be achieved thereby.

On the other hand, RIA procedures do have some shortcomings which make the use thereof impractical for some types of testing and in some environments. That is to say, RIA procedures require the detection of radioisotopes utilizing sophisticated instrumentation such as gamma or scintillation counters. Moreover, radioisotopes are inherently unstable and have limited shelf life. Additionally, radioisotopes are hazardous and the use thereof is limited to specially trained technicians and laboratories equipped with hazardous waste disposal procedures and facilities.

The shortcomings inherent in RIA procedures have been overcome through the use of non-radioactive labels or markers such as enzyme color formers, fluorescent materials, chemiluminescent markers, etc. When an enzyme is employed as the label, the assay methods have come to be known as enzyme immunoassays (EIA) or enzyme linked immunosorbent assays (ELISA) wherein a solid phase immunosorbent is employed. Commonly, such enzymes as horseradish peroxidase, alkaline phosphatase, glucose oxidase and urease have been employed as labels. These enzymes react with specific substrates to produce a detectable signal, usually production of color, which can be quantitated with somewhat simpler instrumentation, for example colorimeters, than is needed in connection with RIA procedures. Moreover, the use of enzymes presents little or no hazard when compared with radioisotopes.

Most enzyme systems useful in connection with EIA or ELISA procedures are relatively stable and can often be stored under refrigerated conditions for as much as a year or so. As a result, assay procedures utilizing enzyme markers are extensively employed today in a variety of laboratory settings and in some cases in physician's offices and even in the home of the users. Other procedures such as fluorescent and chemiluminescent assays likewise overcome the stability and hazard drawbacks of RIA. However, these procedures generally require sophisticated instruments so that the use thereof is limited primarily to well equipped laboratories. A number of enzyme, fluorescent and chemiluminescent labels useful in immunoassay procedures are disclosed in U.S. Pat. No. 4,233,402.

Generally speaking, enzyme labelled immunoassay procedures have been utilized to satisfy the need and desirability for highly sensitive and specific immunoassays conducted at remote sites. The remote sites where such testing is desirably conducted, as referred to above, include the physician's office and the home of the user. In the physician's office, it is often useful for rapid, simple assays to be performed while the patient is still in the office so that diagnosis may be accomplished without delay and treatment instituted during a single visit. Without such assays, it is often necessary for the physician to collect a sample from the patient during a first visit, such sample then being sent to a clinical laboratory for analysis with the results being reported back to the physician by the laboratory at a later time. In the meanwhile, the patient is sent home and must return for a second visit with the physician in order to receive appropriate treatment and/or medication. Such delay is inefficient and inappropriate and in some cases may even be life threatening.

Home testing is desirable to facilitate testing by the consumer in the privacy of his or her own home. The results of the test may indicate the necessity or lack of necessity of a visit to a physician. Examples of useful tests for the "at home" market are tests for pregnancy, ovulation, streptococcus infection and other infections which may be detected by analysis of urine, saliva or other appropriate test samples.

For remote site testing, assuming appropriate sensitivity and specificity can be achieved, there are at least three other requirements for practical assay procedures. The first of these desirable factors is speed in that the assay must be performed in an acceptably short period of time, the shorter the better. Stability is also a desirable feature in that the components of the assay should be stable for an extended period of time without refrigeration or special handling and the assay results or readout should be sufficiently stable so that the interpretation may be confirmed even several days after the initial test has been performed. Finally, from a commercial view point, it is desirable that the test be as simple as possible requiring only minimal or no instrumentation and precluding mistakes and poor performance resulting in incorrect interpretations.

Immunoassay kits employing enzyme markers are available commercially today for determining pregnancy and ovulation. The technical components generally included in such kits are (1) a solid phase bearing immobilized antibody, (2) an enzyme labelled antibody, (3) a rinse solution (in some cases this may be the user's tap water), and (4) a substrate for the enzyme. A typical procedure is that the sample is mixed with the solid phase and incubated (with or without a subsequent rinse step) and then the sample is discarded. The solid phase is then contacted with the enzyme labelled antibody and incubated and thereafter the solid phase is rinsed and contacted by the substrate. After a period of time (ca. 5 minutes) the color of the solid phase is observed One such assay is described in U.S. Pat. No. 4,632,901.

Enzyme labelled immunoassays are not without their own drawbacks resulting from the instability of sole enzyme systems, the number of kit components and the complexity of the procedure. As a result, work continues in an effort to simplify, increase the speed of and provide stability for the components and products of immunoassay procedures, particularly procedures to be conducted at remote sites. One result of such work was the recognition of metal sol particles as a marker in an immunoassay procedure. Such procedure is disclosed in U.S. Pat. No. 4,313,734. In this patent disclosure, protein coated metal sol particles react with a protein coated solid phase to cause a change in optical properties and provide a colorimetric determination in the liquid phase. The immunological reaction results in an agglutination or agglomeration of dispersed materials, an occurrence which brings about changes in the light absorption and reflection characteristics of the liquid phase. Such changes are measured using instruments such as spectrophotometers. In some cases, the color change in the liquid phase is such that it may even be assessed visually by comparison of the coloration in the sample with the coloration of control liquids, and even perhaps by observing subtle color changes in the fluid as the coloration changes from red to purple to colorless. The course of the reaction in an agglutination test is time dependent and the visual determinations must be made at a particular point in time. Moreover, the test results generally lack stability since the reaction continues even after visual assessment is made.

Agglutination resulting from the reaction of immunoreactive reagents and utilizing gold as a label was also used for the detection of mannan by Horisberger and Rosset, in their work described in their article entitled "Colloidal Gold, A Useful Marker For Transmission And Scanning Electron Microscopy", *J. Histochem. Cytochem.* 25, 1977, pp. 295-305. In this work, an agglutination process was employed and the course of the immunoreaction was followed by spectrophotometrically reading the absorbance of light in the fluid. This work provided a prelude for the work described in the '734 patent.

Another prior procedure which utilized protein coated particles is described in U.S. Pat. No. 4,115,535. The procedure described in the '535 patent involves an immunological process which results in agglutination of two different kinds of particles coated with the same protein. One of the particles has magnetic properties so that the agglutinated mass may be separated from the liquid with a magnet. The other kind of particle is described as consisting of fluorescent and/or distinctively colored small polymer particles. The size of each of the particles is specified as being one micron or less. Although metal particles are used as magnetic particles, there is no suggestion in this disclosure of the use of metal particles to provide a colorimetric result. Agglutination is also involved in the procedure disclosed in U.S. Pat. No. 4,486,530.

An interesting prior art procedure is disclosed in the published *Abstracts of the Annual Meeting* - 1986 of the International Congress of Immunology, at page 363 (Abstract C-213). This procedure involves the use of antibodies immobilized on a nitrocellulose membrane. The antibodies are used to capture antigens during immunofiltration of the specimen through the membrane. Thereafter the membrane was stained with colloidal gold conjugated antibodies. A red spot was said to indicate a positive reaction. This procedure suffers from the same sort of defect as the enzyme immunoassay procedures described above in that two pouring steps are required and the procedure requires the prior preparation and use of a membrane to which specific antibodies are bound.

SUMMARY OF THE INVENTION

The present invention provides relief from the shortcomings of the prior art procedures described above. In this regard, the invention provides a simplified, sensitive and specific test procedure which utilizes stable components and provides a stable test result. In accordance with the present invention, a process is provided for the determination and detection of an immunologically reactive analyte in an aqueous sample. The process involves the provision of a labelled component comprising the coupling product of an immunologically reactive substance and a metal-containing particle of a size and character to facilitate the maintenance of a generally stable, monodispersed suspension of the labelled component. Also provided is a solid phase component which comprises the coupling product of an immunologically reactive substance and a solid phase particle of a size and character to facilitate the maintenance of a generally stable suspension of the solid phase component. The solid phase component and the labelled component are mixed together and brought into contact with the sample to be analyzed so as to form a single mixed aqueous suspension containing the components and the sample to be analyzed for analyte. The immunologically reactive substances coupled to the particles are capable of binding directly or indirectly as a function of the presence of analyte to thereby form a dispersed, collectable, solid phase, metal-containing composite. The procedure includes the final step of collecting the composite and determining or detecting the analyte in the sample by evaluating, through direct visual examination, the presence of metal in the collected solid phase composite.

The procedure is useful in the determination and detection of immunologically reactive analytes generally and in particular analytes which are ligands or anti-ligands, the latter being sometimes referred to as ligand receptors. And in the more specific aspects of the invention, the metal-containing particles are preferably metal sol particles having a particle size in the range of from about 50 Angstroms to 1000 Angstroms and even more preferably, in the range of from about 135 to about 500 Angstroms. In a particularly preferred form of the invention, the process involves the use of gold sol particles.

The labelled component utilized in the procedure of the present invention may be prepared by coupling an immunologically reactive substance directly to the particle. Additionally, the labelled component may be prepared by coupling the substance to the particle using a biotin/avidin linkage. In this latter regard, the substance may be biotinylated and the metal containing particle coated with an avidin compound. The biotin on the substance may then be reacted with the avidin compound on the particle to couple the substance and the particle together. In another alternative form of the invention the labelled component may be prepared by coupling the substance to the particle using bovine serum albumin (BSA).

In accordance with the invention, the solid phase component may also be prepared by coupling the corresponding substance directly to the solid phase particle. Alternatively, the solid phase component may be prepared by coupling the substance to the particle using a BSA linkage. And in yet another alternative form, the solid phase component may be prepared by coupling the substance to the particle using gelatin.

In accordance with one preferred form of the invention, the immunologically reactive substances may both be capable of binding the analyte to form a sandwich. In this regard, the substances may each be antibodies capable of immunologically binding an antigen analyte. Preferably, such antibodies bind respective different sites on the antigen.

In another preferred form of the invention, the immunologically reactive substances may bind each other, that is to say, one of the substances may be an antibody and the other may be an antigen. Preferably, the immunologically reactive substance of the labelled component will be the antibody. In this form of the invention, the assay procedure may rely on a competitive inhibition procedure.

In one preferred aspect of the invention, the collection step may comprise capturing the composite on the surface of a porous filtration element which permits passage of filtrate but prevents passage of the composite. In this aspect of the invention, the filtrate may be pulled through the element by gravity or by centrifugal or capillary force. In another aspect of the invention, the collecting step may consist of causing the composite to gravitate into a limited volumetric space by sedimentation to thereby form a concentrated pellet. In another aspect of the invention, the collecting step may comprise subjecting the aqueous suspension to centrifugation to force the composite into a limited volumetric space and thereby pack the same into a dense pellet.

In another important aspect, the invention provides a kit of materials for use in determining and detecting an immunologically reactive analyte in an aqueous sample. The kit may include, for example, a labelled component comprising the coupling product of an immunologically reactive substance and a metal-containing particle of a size and character to facilitate the maintenance of a generally stable, monodispersed suspension of the labelled component; a solid phase component comprising the coupling product of an immunologically reactive substance and a solid phase particle of a size and character to facilitate the maintenance of a generally stable suspension of the solid phase component, said components being operable and co-operable to permit formation therefrom of a mixed aqueous suspension of said components and which contains a sample to be analyzed for the analyte, the substance of said labelled component and the substance of said solid phase component being capable of binding directly or indirectly as a function of the presence of analyte in the sample to thereby form a dispersed, collectible, solid phase, metal-containing composite; and a collector element for collecting and permitting direct visual examination of the composite for the purpose of evaluating the presence of metal in the solid phase composite to thereby detect or determine the original presence of analyte in the sample.

In yet another of its aspects, the invention provides a stable collected mass of a solid phase, metal-containing composite capable of being directly visually observed to indicate the initial presence, absence or amount of an analyte in an aqueous sample. The composite comprises a labelled component which is the coupling product of an immunologically reactive substance and a metal-containing particle of a size and character to initially facilitate the maintenance of a generally stable, monodispersed suspension of the labelled component; a solid phase component comprising the coupling product of an immunologically reactive substance and a solid phase particle of a size and character to initially facilitate maintenance of a generally stable suspension of the solid phase component, said substances being directly or indirectly bound to each other to present said composite. In this aspect of the invention, the mass is collected on a porous filter element or at the bottom of a test tube. In such form the collected composite is relatively stable colorwise and may be retained for confirmation of results at a later time.

DETAILED DESCRIPTION OF THE INVENTION

In accordance with the concepts and principles of the present invention, metal sol particles having a particle size in the range of from about 50 to about 1000 Angstroms may be coated with antibodies. Such metal particles, and in particular gold sol particles with antibodies coated on their surface have already been described by M. Horisberger et al. in *Experimentia*, 31, pp. 1147–1149, 15 October, 1975. Such gold particles coated with antibody or antigen are intensely colored, either orange, red or violet, depending on particle size.

In accordance with the present invention, and quite unexpectedly, it has been found that in many immunoassays which normally employ enzymes as color formers, gold labelled immunoreactants may be directly substituted for the enzyme labelled immunoreactants without significant loss of sensitivity. This is a most important finding since gold labelled antibodies are, under the conditions described below, directly visualizable with the naked eye, whereas detection of enzyme labelled antibodies requires addition of substrate for that enzyme. Metal sol assays, and in particular gold sol assays, therefore, require one less step and one less reagent. In addition, colloidal gold particles are in general, considerably more stable than most enzyme labelled antibodies.

In accordance with the procedure of the present invention, gold particles coated with an immunoreagent are mixed with a suspension of solid particles such as latex, silanized glass, Sepharose, Reactogel or isothiocyanate activated glass, which solid particles are also coated with an immunoreagent. Such mixed suspension is contacted by a sample containing an analyte that is bindable to either or both of the immunoreagents bound to the gold sol phase and the suspended solid phase. The gold particles are then immunospecifically linked to the solid phase (sandwich mode) or anticipated linkage is prevented (competitive inhibition mode). Various embodiments of this concept are described hereinbelow.

In each of the embodiments and examples described herein, a suspended solid phase is collected, or harvested, or captured, by sedimentation, centrifugation, or entrapment on and within a porous capture matrix. The assay results are obtained by direct visual examination of the captured solid phase. If gold sol particles are employed, then the captured solid phase will be either intensely red, pink or essentially colorless, depending on the presence of the analyte and assuming that the solid phase is itself colorless in the absence of the gold sol particle.

The metal sol particles to be used in accordance with the present invention may be prepared by methodology which is known. For instance, the preparation of gold sol particles is disclosed in an article by G. Frens, *Nature*, 241, 20–22 (1973). Additionally, the metal sol particles may be metal or metal compounds or polymer nuclei coated with metals or metal compounds, all as described in the '734 patent mentioned above. In this regard, the metal sol particles may be of platinum, gold, silver or copper or any number of metal compounds which exhibit characteristic colors.

The solid phase particles may comprise any one of a number of known, water dispersable particles, such as, for example, the polystyrene latex particles disclosed in U.S. Pat. No. 3,088,875. Such solid phase materials simply consist of suspensions of small, water-insoluble particles to which proteins, such as the immunologically reactive substances of the present invention, are able to bind. Suitable solid phase particles are also disclosed, for example, in U.S. Pat. Nos. 4,184,849; 4,486,530; and 4,636,479.

The solid phase particles useful in connection with the invention may comprise, for example, particles of latex or of other support materials such as silica, agarose, glass, polyacrylamides, polymethyl methacrylates, carboxylate modified latex and Sepharose. Preferably the particles will vary in size from about 0.2 microns to about 10 microns. In particular, useful commercially available materials include 0.99 micron carboxylate modified latex (Polysciences), cyanogen bromide activated Sepharose beads (Sigma), fused silica particles (Ciba Corning, lot #6), isothiocyanate glass (Sigma), Reactogel 25DF (Pierce) and Polybead - carboxylate monodisperse microspheres (Polysciences). In accordance with the invention, such particles may be coated with a layer of immunologically reactive substances coupled thereto in a manner known per se in the art to present the solid phase component.

Either monoclonal or polyclonal antibodies may be employed, in accordance with the invention, for detecting or determining specific antigens. Monoclonal antibodies which are useful may be prepared in accordance with the discovery of Milstein and Kohler cited above Monoclonal antibodies which are particularly desirable in accordance with the present invention may be prepared using the polyethylene glycol (PEG) promoted hybridization method of Gefter, Margulies and Scharff reported in *Somatic Cell Genetics*, Vol. 3, No. 2, 1977, pp. 231–236. Suitable antibodies useful in detecting human choriogonadotropin (hCG) and human leutenizing hormone (hLH) may be prepared using a slightly modified Gefter et al. procedure involving immunization of strain A mice (Jackson Laboratories, Bar Harbor, Maine) with either hLH or hCG utilizing any one of a variety of known immunization schedules, antigen doses and modes of antigen presentation. Such procedures induce the production of antigen reactive serum antibodies capable of successfully producing hybridoma cell lines. In particular, hybridomas were prepared by fusing Sp6 mice lymphocytes from immune mice with SP2/0-Ag14 cells, see M. J. Shulman and G. Kohler, *Nature*, Vol. 274, pp 917–9 (1978), via the polyethylene glycol catalyzed cell fusion procedure of Gefter et al. Hybridoma tissue culture supernatants were initially assayed by means of a solid phase antigen binding immunoassay in accordance with the method of Klinman et al. (Klinman, N. R., Pickard, A. R., Sigal, N. H., Gearhart, P. J., Metcalf, E. S. and Pierce, S. K., *Ann. Immunol. (Inst Pasteur)*, Vol 127 C, pp 489–502 (1976)).

After assaying and screening using conventional procedures, hybridoma cell lines for producing antibodies having appropriate binding efficiencies and specificities were identified. The antibodies produced using such hybridoma cell lines are identified, for convenience, using the terminology 2B2 for a hCG specific antibody, LH26 for a hLH specific antibody and HCG/KLH/2G9 for an antibody which reacts specifically with both hLH and hCG. The 2B2 antibody binds selectively to one discrete binding site on the hCG antigen molecule while the HCG/KLH/2G9 antibody binds selectively to a separate, discrete binding site on the hCG molecule. Likewise, the LH26 and HCG/KLH/2G9 antibodies bind selectively to separate, respective, discrete binding sites on the hLH molecule.

The list of target ligands and anti-ligands which potentially may be detected or determined in accordance with the present invention is too long for inclusion here. However, suffice it to say, that ligands and antigens such as IgE, hCG, hLH, pregnanediol-3-glucuronide (P3G) and other antigens and ligands found in animal body fluids, as well as antigens associated with bacteria, parasites, fungi or viruses such as streptococcus, chlamydia or gonorrhea, for example, may be detected and determined by the method of the invention. Moreover, therapeutic drugs and controlled substances having small molecules, such as, for example, theophylline, may be detected or determined using the present invention.

The invention is further illustrated by way of the following examples.

EXAMPLES

Example I

Gold Sol Preparations (a) Gold sol particles are prepared in accordance with the method of Frens (1973) referred to above. In general, 0.2 grams of chlorauric acid (HAuCl$_4$) (AESAR, Seabrook, New Hampshire) is dissolved in two liters of 19 megaohm deionized distilled water and brought to a boil within 30 minutes. 48 ml of a fresh solution of 1% trinatrium citrate is rapidly added while stirring. Within 5 minutes, a brilliant orange sol dispersion is formed. An optical scan of the resulting material revealed maximum absorbance at 520 nanometers (nm). The diameter of the obtained particles was determined by viewing with a scanning electron microscope and found to be approximately 135 Angstroms (A).

(b) Gold sol particles having a diameter of 500 A are prepared using the procedure of Example I(a) except that 15 ml of the trinatrium citrate solution are added rather than 48 ml.

EXAMPLE II

Gold Probe Preparation

The optimal conditions for coating proteins onto gold sol particles differ from protein to protein and from batch to batch of the gold sol particles. And such conditions must in general be determined empirically. To determine the optimum conditions, proteins to be absorbed to the gold sol particles are first exhaustively dialyzed at room temperature against 2 millimolar (mM) borate-10 mM azide solution having a pH of 8.0. Prior to coating, the dialyzed preparation is filtered through a 0.20 micrometer (um) Millex GV filter (Milipore, Bedford, Massachusetts). The protein concentrations are determined spectrophotometrically using an extinction coefficient of 1.4. To determine the quantity of protein needed for optimum coating of gold sol particles, pH and protein concentration variable isotherms are constructed. The method of Goodman, Hodges, Trejdosiewicz and Livingston, *Journal of Microscopy*, Vol. 123, Pt. 2, August, 1981, pp. 201-213, is used with some modifications, as indicated hereinafter. The effect of pH on the absorption of protein on gold particles is examined in a series of eleven different buffers having pHs ranging from 2.3 to 11.0. The buffers used, in order of increasing pH, are tris, sodium phosphate, sodium carbonate, citric acid, boric acid, barbital, piperazine, morpholine, lactic acid, sodium salicylate and phthalic acid. For spectrophotometric analysis, 270 microliters (ul) of gold sol is added to 30 ul aliquots of 70 mM buffer containing 10 mM concentration of azide. These solutions are vortexed and allowed to remain at room temperature for 15 minutes. 60 ul of a 50 microgram (ug) per ml protein solution is then added while vortexing. After standing for one hour at ambient temperature, 60 ul of a 10% sodium chloride solution is added. The absorbance is measured at the maximum absorbance (525 nanometers(nm)) for the unflocculated sol. The reaction is also scored visually since the sol is originally orange/red and the color changes to blue/gray upon flocculation. Exploiting this property of colloidal gold, the optimum buffer is selected in accordance with the Goodman et al. procedure. A protein concentration isotherm may be determined in a similar manner using concentrations ranging from 1 mg per ml to 3.9 mg per ml. In this way, an optimum buffer and adsorptive protein concentration may be selected for each combination of protein material and gold sol batch. The effects of overadsorption of protein may also be explored using preparations of probes at protein concentrations above and below the optimal coating levels. Optimally coating gold sol particles are prepared in accordance with the foregoing methodology and utilized in the following examples.

(a) A gold probe coated with a monoclonal antibody capable of reacting specifically with either human chorionic gonadotropin (hCG) or human leutinizing hormone (hLH), and identified above as antibody HCG/KLH/2G9, is prepared by rapidly admixing 200 ml of 70 mM carbonate-10 mM azide buffer and 1800 ml of a gold sol dispersion preparation in accordance with Example I(a) in a 4 liter beaker. The resulting pH is 9.9. While mixing, 400 ml of a 150 ug/ml antibody solution in a 2 mM borate-10 mM azide buffer having a pH of 8.0 is added and allowed to react for 15 minutes. 180 ml of 5% polyethylene glycol (PEG) 20 M (Sigma, St. Louis) which has been prefiltered through a 5 um Acrodisc (Gelman, Ann Arbor), is then added while mixing and the admixture is allowed to react for 15 minutes at ambient temperature. The probe is then aliquoted into a series of 220 ml Nalgene polycarbonate bottles and placed in a Sorvall GSA rotor and centrifuged at 10,000 rpm in a Sorvall RC5B centrifuge for 45 minutes at 4° C. The supernatants are discarded and the dark red pellets are resuspended in equal volumes of Buffer X which has a pH of 7.3, and consists of 0.1% bovine serum albumin (BSA) (Miles), 0.1 grams per liter (g/l) Thimerosal (Marchem Research), 0.3 g/l sodium chloride and 0.2 g/l PEG 20 M (Sigma). The centrifugation procedure is repeated and the resulting pellets are resuspended in a minimal volume of Buffer X, filtered through 0.2 um Millex GV units (Millipore) and then brought up to a volume of 50 ml, again using Buffer X. The prepared probes are then placed in amber glass bottles and stored at 4° C. prior to use. An aliquot portion diluted 1:20 in deionized water exhibits an absorbance maximum of 525 nm and has an orange/red color.

(b) A probe for pregnanediol-3-glucuronide is prepared by rapidly admixing 598.5 ml of the gold sol dispersion of Example I(a) and 66.5 ml of a 70 mM borate-10 mM azide buffer having a pH of 8.5. 133 ml of a solution containing antibodies to pregnanediol at a concentration of 75 ug/ml and a 2 mM borate-10 mM azide buffer having a pH of 8.0, is added to the buffered gold sol mixture with mixing. The resulting admixture is allowed to react for 15 minutes The material is then centrifuged and handled as set forth above in Example II(a).

(c) Another multipurpose probe for both hCG and hLH is prepared by first coating gold sol particles with streptavidin (Sigma, St. Louis). In this case, 67.5 ml of the gold sol dispersion of Example I(a) and 7.5 ml of an 8.3 pH carbonate buffer are placed in a beaker and subjected to rapid mixing. During the rapid mixing, 15 ml of a solution containing streptavidin at a concentration of 75 ug/ml in a borate buffer, are added. The solution is allowed to mix at ambient temperature for 15 minutes and then 6.75 ml of filtered PEG 20 M is added. After centrifugation and washing, this probe is also handled as specified in Example II(a) above.

The HCG/KLH/2G9 antibody, which is specifically reactive with both hCG and hLH, is biotinylated to facilitate attachment to the streptavidin gold probe. For this purpose, 1 mg of biotin-e-aminocaproic acid N-hydroxysuccinimide ester (Biotin- x-NHS, Cal. Biochem.) is dissolved in 1 ml of DMSO (Aldridge). A solution containing the antibody at a concentration of 1 mg/ml is prepared using 0.1 M sodium bicarbonate buffer to maintain the pH at 8.2. 60, 120 and 240 ul portions of the biotin-X-NHS solution are added respectively to 1 ml aliquots of the antibody solution and reacted for 2.4 hours at ambient temperature. After the incubation, dialysis is performed for 16 hours at ambient temperature against a phosphate buffered saline (PBS)-azide solution at a pH of 7.2. 400 ul aliquots of each sample are then reacted with 156 ul of the avidin coated gold probe. Each sample is allowed to react for 15 minutes at room temperature and then the sample is diluted with 12 ml of Buffer X and centrifuged for 30 minutes at 10,000 rpm in a Sorvall RC5B centrifuge at 4° C. The sample is then filtered through a 0.2 u Millex GV filter and stored at 4° C.

(d) A probe for theophylline is prepared by first conjugating theophylline butyric acid (TBA - Cal. Biochem, 581116) to bovine serum albumin (BSA) by dissolving 110 mg of BSA and 20 mg of TBA in 3 ml of a mixture containing 9 parts water to 1 part pyridine. To this solution, 29 mg of N-ethyl,N-dimethylamino carbodiimide hydrochloride is added. After overnight incubation at room temperature, the mixture is exhaustively dialyzed against PBS, and then stored in 4 ml of PBS.

The TBA-BSA conjugate is coated onto colloidal gold as follows. 8 ml of a gold sol dispersion prepared in accordance with Example I(a) above in a 0.001 M tris buffer is added to 1 ml of 0.07 M tris buffer at a pH of 7.0. 200 ul of the resultant TBA-BSA conjugate solution is diluted with 3 ml of PBS and the resulting admixture is added dropwise to the buffered colloidal gold solution while the latter is vortexed. 30 ml of PBS are then added and the mixture is centrifuged at 27,000 G for 20 minutes. The pellet is resuspended and similarly washed 6 times by centrifugation. The theophylline coated gold sol is finally resuspended in approximately 3 ml of PBS containing 0.1% BSA.

(e) A gold probe coated with a monoclonal antibody capable of reacting specifically with either hCG or hLH is prepared using the procedure of Example II(a), except that in this case the gold sol dispersion is prepared in accordance with Example I(b) and the antibody solution has an antibody concentration of 300 ug/ml. The prepared 500 A gold probe particles are filtered, washed, handled and stored as set forth in Example II(a).

EXAMPLE III

Preparation of the Solid Phase Components (a) 1.0 ml of 0.99 u carboxylate modified latex (Polysciences) and 20 ml of a 0.15 M NaCl solution are placed in a centrifuge tube. 0.75 ml of a water solution of 1-ethyl-3-(3-dimethylaminopropyl) carbodiimide hydrochloride at a concentration of 100 mg/ml is added to the centrifuge tube and the admixture is stirred for 20 minutes. Thereafter, 11 ml of a 0.15 M NaCl solution is added and this mixture is sedimented at 38,000 G for 10 minutes. The supernatant is discarded and the pelleted latex particles are resuspended in 20 ml of the 0.15 M NaCl solution. The suspension is re-centrifuged as above and the pellet finally resuspended in 4 ml of the 0.15 M NaCl solution. 2 ml of this latex suspension, 1.5 ml of the 0.15 M NaCl solution and 1.5 ml of a solution containing hLH specific antibody (identified above by the designation LH26) at a concentration of 1.678 mg/ml, are mixed in a 15 ml plastic test tube. The tube is capped and the mixture is incubated with end over end stirring on a Labquake rotator for 16 hours at 22° C. Thereafter, 1.0 ml of a 1 M lysine solution having a pH of 7.5 is added and the mixture is stirred for an additional 30 minutes. The antibody coated latex is then washed four times with 30 ml of 0.15 M NaCl solution with repeated pelleting as set forth above. The final pellet is resuspended in 2 ml of 0.15 M NaCl solution containing 1 mg/ml of BSA.

(b) Rabbit anti-theophylline anti-serum is obtained from Kallestad Laboratories, Chaska, Minnesota (Catalog No. 334, Lot No. X3531). The gamma globulin fraction of the serum is obtained by addition of ammonium sulfate to a final concentration to 40%, centrifugation, redissolution in PBS and dialysis against PBS. 0.2 ml of this preparation, at a protein concentration of 23 mg/ml, is reacted with 0.5 gm of cyanogen bromide activated Sepharose beads (Sigma Chemical Co.) which are suspended in 2 ml of a 0.15 M NaCl, 0.059 M. NaHCO$_3$ solution. After mixing for 2 hours at room temperature, the reaction is stopped by addition of 2 ml of a 0.27 M lysine solution having a pH of 8.4. The polyclonal antibody coated beads are then collected on a sintered glass filter, washed with 0.15 M NaCl and stored in isotonic saline.

(c) A cyanogen bromide Sepharose/antibody to hCG preparation was prepared as follows. 1.0 gram of cyanogen bromide Sepharose 4B beads (Sigma) is washed on a sintered glass filter with 200 ml of 0.0001 M HCl. The washed beads are then added to a tube containing 3 ml of PBS containing 9.0 mg of the hCG specific antibody identified above by the designation 2B2. The tube is capped and the mixture is then rotated end over end overnight at room temperature. The reaction is terminated by the addition of 100 mg of lysine in 2 ml of water at a pH of 8.1. Mixing is continued for another 30 minutes by manual shaking and the suspension is then filtered onto a sintered glass filter and repeatedly washed with a 0.15 M NaCl solution. The hCG antibody coated beads are then resuspended in 4 ml of isotonic saline.

(d) An antibody to hCG coated isothiocyanate glass solid phase preparation is prepared by mixing 0.127 gm of isothiocyanate glass beads (Sigma) with 3 ml of a solution of the 2B2 antibody at a protein concentration of 2.886 mg/ml. The antibody solution is buffered with a borate buffer to a pH of 9.0 and the admixture is subjected to end over end mixing overnight at room temperature. The reaction is stopped by the addition of 1 ml of a lysine:HCl solution having a lysine concentration of 40 mg/ml and a pH of 8.1. After one hour of mixing, the suspension is filtered onto sintered glass and washed with a 0.15 M NaCL solution. The 2B2 antibody coated glass beads are then stored in 3 ml of a 0.15 M NaCl solution.

(e) A Reactogel-antibody to hCG preparation is prepared by coupling 0.15 grams of Reactogel 25DF (Pierce Chemical) to the 2B2 antibody using precisely the same procedure as outlined above for isothiocyanate glass in Example III(d).

(f) A fused silica glass antibody to hCG solid phase is prepared as follows. Fused silica particles (Ciba Corning, lot #6) are silanized by suspending 10 gm of the silica particles in 40 ml of water and adding 10 ml of 3animopropyltriethoxysilane (Eastman Kodak Company, Catalog No. 8746, Lot No. C14D). This mixture is rotated end over end in a sealed tube for 4 hours at room temperature. The silanized particles are then washed 6 times with 50 ml of water per wash and centrifugation at 1,500 G for 10 minutes. 100 mg of the aminoalkylsilanized particles are suspended in 2 ml of a water solution containing 2.5% glutaraldehyde. This mixture is rotated end over end in a sealed tube for 4 hours at room temperature. The particles are then harvested by centrifugation at 1,500 G for 10 minutes. The resulting pellet is resuspended in 2 ml of a solution containing the 2B2 hCG specific antibody at a protein concentration of 3.5 mg/ml. This suspension is rotated end over end for 4 hours. The particles are then harvested by centrifugation as before and resuspended in 2 ml of a solution containing the 10 mg/ml of BSA in PBS. This suspension is also rotated end over end for 1 hour harvested and the particles resuspended in 2 ml of PBS containing 1 mg/ml of BSA.

(g) Pregnanediol-3- glucuronide (P3G) (Sigma) in the free acid form is covalently coupled to gelatin (Sigma) by the mixed acid anahdride method, exactly as described by Erlanger et al., J. Biol. Chem. 228, 713-727 (1957). 1 ml of Polybeadcarboxylate monodisperse microspheres (Polysciences) is mixed with 10 ml of PBS and 11 mg of 1-ethyl-3-(3-dimethylaminopropyl) carbodiimide hydrochloride (Sigma) is then added to the mixture. After 10 minutes of incubation with end over end mixing in a sealed test tube at 22° C., the latex suspension is centrifuged at 10,000 rpm in a Sorvall RC5B centrifuge equipped with an SS-34 rotor and the supernatant is discarded. The pellet is resuspended in 10 ml of PBS containing 8.9 mg of gelatin P3G. This mixture is incubated with end over end stirring for 12 hours at 22° C. 1 ml of lysine hydrochloride in water at a concentration of 10 mg/ml is then added to block unreacted binding sites and after 10 minutes, the antibody coated particles are harvested by centrifugation as described above. After twice washing the pellet in this manner, the antibody coated latex particles are finally resuspended in 5 ml of PBS.

(h) A solid phase component consisting of latex particles coated with hCG specific antibody is prepared using the exact procedure detailed in Example III(a) except that in this case, 1.5 ml of a solution containing the 2B2 hCG specific antibody at a concentration of 1.678 mg/ml is used in place of the solution of hLH specific antibody.

EXAMPLE IV

Assay Formats (a) The gold probes containing absorbed avidin coupled to biotinylated hCG/KLH/2G9 antibody and having various biotin to antibody ratios, all as prepared in accordance with Example II(c) above, are evaluated in an assay procedure. In this procedure, 6 assay tubes are prepared containing 0.5 ml of a buffer solution consisting of a 0.3 M concentration of NaCl, a 0.1 M concentration of a 7.2 pH HEPES buffer and 1% polyvinylpyrrolidone (PVP) (360,000 molecular weight). Three of the tubes also contain 200 mIU LH per ml while the remaining assay tubes contain no LH. Thereafter, 0.020 ml of a latex suspension containing dispersed latex particles coated with covalently attached LH specific antibody prepared in accordance with Example III(a) and 0.150 to 0.175 ml of the gold probes prepared in accordance with Example II(c) are added to each tube. The resultant admixtures, each containing a dispersed solid phase component comprising the antibody coated latex particles and a labelled component comprising the antibody coated gold probe particles, have orange/red colorations. The samples are incubated at room temperature for 10 minutes during which time the color in the tubes does not change, and then each sample is vacuum filtered with a 1 u RC60 Schleicher and Schuell filter housed in a Schleicher and Schuell SRC-96 manifold. After filtration of the samples, each is washed with 0.5 ml of 1% Igepal CA-720 (GAF) containing 1% SDS. The filter is air dried and the intensity of the color of the entrapped particles retained an the 1 u filter is quantitated both visually and with a reflectance spectrophotometer (Macbeth, Kollmorgen Corporation). The results are set forth below in Table I.

TABLE I

| Gold probe ratio of biotin NHS:antibody | mIU/ml lH | Reflectance Spectroscopy | Visual |
|---|---|---|---|
| 60 ug:mg | 0 | 0.45 | +1 |
|  | 200 | 3.59 | +3 |
| 120 ug:mg | 0 | 0.85 | +1 |
|  | 200 | 3.99 | +3 |
| 240 ug:mg | 0 | 0.51 | +1 |
|  | 200 | 2.48 | +2 |

As can be seen from the foregoing, the presence of LH in the sample is determined and detected by evaluating, through direct visual examination, the presence of metal in the collected solid phase composite. The metal produces a coloration on the filter which can be visually ascertained and such color indicates that the metal is there. As another result of the foregoing assay procedure, it is determined that better visual results are obtained using lesser ratios of biotin to antibody. This result is determined both directly and through the use of the reflectance spectroscope.

(b) A competitive sedimentation assay for theophylline is conducted in the following manner. The antibody coated Sepharose suspension prepared in accordance Example III(b) above, is resuspended by shaking the same immediately before use and 40 ml thereof is added to each of a series of conical plastic tubes (Falcon 2097). Solutions containing theophylline at various concentrations are added to the tubes and after mixing and incubation for 2 minutes at room temperature, 250 ul of a theophylline-BSA gold sol dispersion prepared in accordance with Example II(d) above are added to each tube and the contents are mixed by shaking for 4 minutes. The beads are then allowed to settle for approximately 30 minutes and the coloration of both the settled beads and the supernatant in each tube is evaluated visually. In the tubes containing more than 0.1 ug of theophylline, the beads are essentially white and the supernatant is distinctly pink. In the tubes containing less than 0.1 ug of theophylline, however, the beads are increasingly pink as theophylline concentration decreases. At the same time the supernatants are increasingly clear. The results are also evaluated by measuring the absorbance of the supernatant with the following results.

TABLE II

| Amount of theophylline in tube | Absorbance at 540 nm of supernatant |
| --- | --- |
| .0001 ug | .046 |
| .001 ug | .049 |
| .01 ug | .064 |
| .1 ug | .104 |
| 1.0 ug | .109 |
| 10 ug | .109 |
| 100 ug | .109 |

As can be seen, the results are consistent with competitive assays generally in that increased levels of theophylline in the test sample results in a decreased presence of labelled theophylline in the solid phase. That is, the theophylline in the sample inhibits the binding of the labelled theophylline to the solid phase. Accordingly, as is determined by direct visual observation, increased concentrations of theophylline in the samples results in less color in the collected solid phase and more coloration in the supernatant.

(c) A gravity separation assay for hCG is conducted as follows. In this procedure, 50 ul of hCG specific antibody coated Sepharose particles, prepared in accordance with Example III(c), 300 ul of antibody coated gold sol particles prepared in accordance with Example II(a), 100 ul of one of several standard solutions containing different amounts (1, 10 or 100 ng) of hCG and 300 ul of PBS-BSA buffer, are added to each of a series of conical plastic tubes. After 30 to 3 minutes of rotary mixing, the beads are allowed to settle to the bottoms of the tubes. After settling, the colorations of the beads are observed by direct visual inspection. The solid phase coloration is essentially white in those tubes where the amount of hCG is 1 nanogram (ng). However, in those tubes where the amount of hCG is 10 ng the bead coloration is pale pink, and in those tubes initially containing 100 ng of hCG, the beads have a strikingly pink coloration. Accordingly, the presence of hCG in the samples and the amount thereof is determined and detected by evaluating, through direct visual examination, the coloration resulting from metal bound in the collected solid phase composite. Of course, the pale pink and strikingly pink colorations results from the presence of gold in the collected solid phase metal-containing composite which settles to the bottom of each tube during these assay procedures.

(d) 100 ul of the antibody coated isothiocyanate glass particles prepared in accordance with Example III(d) are added to the respective tubes of a series of conical plastic tubes. 20 ul of the antibody coated gold particles prepared in accordance with Example II(a), 400 ul of PBS-BSA buffer and 100 ul of a solution containing either 1000, 100, 10, 1 or 0 ng/ml of hCG is added to each tube. The tubes are capped and mixed by end over end rotation at room temperature for 1 hour. Thereafter, after settling, the color of the beads is observed by direct visual inspection. The procedure is repeated using antibody coated Reactogel 25DF particles prepared in accordance with Example III(e). Sensitivity of the assay to 10 ng levels of hCG in a tube is noted in the case of the isocyanate glass particles as well as the Reactogel particles, much the same as is found for the cyanogen bromide Sepharose beads in accordance with Example IV(c) above. Again, the antibody coated gold particles and the antibody coated solid phase particles react with the antigen to produce a dispersed, collectible, solid phase, metal-containing composite which is collected by gravitation. The presence and amount of hCG in the original sample is evaluated by a direct visual examination of the coloration caused by the presence of metal in the collected solid phase composite. In each case, the presence of metal in the composite causes the pink coloration of the beads when the initial level of hCG in a tube is 10 ng or more.

(e) The presence of hCG is also detected and determined in a procedure wherein centrifugal force is utilized for collecting the composite. 200 ul of PBS-BSA buffer, 25 ul of respective solutions containing 25, 2.5 or 0 ng of hCG, 20 ul of antibody coated gold sol particles prepared in accordance with Example II(a) and 10 ul of antibody coated fused silica particles prepared in accordance with Example III(f) are added to the wells of a 96 well microtiter plate (Dynatech, Immunlon). After incubation for 5 minutes, the plate is centrifuged at 2000 rpm in an IEC PR2 centrifuge equipped with a 276 rotor. The supernatants are discarded and the pellets are washed with 200 ul of PBS. The final pellets are examined by direct visual observation by placing the plate against a white background. Essentially white pellets are observed in the absence of hCG in the original sample, while distinctly pink or red pellets are produced in those wells which originally contained either 2.5 or 25 ng of the hCG antigen.

(f) A porous matrix capture assay for hCG is conducted as follows. In this procedure 2 assay tubes are prepared, each containing a mixture of 50 ul of the hCG specific antibody coated latex particles prepared in accordance with Example III(h), 300 ul of antibody coated gold sol particles prepared pursuant to Example II(a) and 300 u of PBS-BSA buffer. One of the tubes also contains 100 ul of a standard solution containing 50 mIU of hCG per milliliter, while the other also contains 100 ul of a standard solution containing no hCG. The resultant admixtures, each containing a dispersed solid phase component comprising the antibody coated latex particles and a labelled component comprising the antibody coated gold probe particles, have orange/red colorations. The mixtures in the tubes are incubated at room temperature for 10 minutes during which time the color in the tube does not change. The samples, are poured onto a glass fiber filter (Whatman GF/A) matrix mounted in a self contained flow device as described below. A distinctively pink colored visually apparent spot appears on the matrix at the point contacted by the solution containing the hCG. No such spot appears where the matrix is contacted by the solution containing no hCG. The spotted matrix is shaded from light for four days and the pink spot retains its original intensity. Similar spots have been retained in notebooks for 6 to 12 months and are still highly recognizable.

(g) Another porous matrix capture assay for hCG is conducted using a procedure identical to that of Example IV(f), except that the gold probe of Example II(f) is used rather than the gold probe of Example II(a). In this case, the solutions initially have a dark purplish coloration and the colored spot which develops at the point where the solution containing the hCG contacts the capture matrix has a pink-purplish color. Otherwise the results are the same as obtained in Example IV(f).

(h) A competitive sedimentation assay for P3G is conducted using the gold probe of Example II(b), the solid phase Example III(g) and the procedure of Example IV(b). The observed results are essentially the same as in Example IV(b) in that the beads are increasingly pinker and the supernatants are increasingly clearer as the P3G concentration decreases.

A porous matrix capture format similar to that illustrated and described in Example IV(f) above may eventuate as the most important commercial format for the present invention. In the porous matrix capture format, the dispersed, collectible, solid phase, metal containing composite, irrespective of the solid phase component it contains, is captured on the surface of and in the interstices and pores of the porous matrix. To facilitate the matrix capture process in the laboratory, a self contained flow device has been constructed which serves to hold the capture matrix in tight contact with an absorbent so that the flow of liquid through the capture matrix is spontaneous and does not require a vacuum or external pressure source. The absorbent media which has been found to be most useful in the laboratory is a Transorb (American Filtrona) unit consisting of a cellulosic plug. It has been found that when a separator is placed between the capture matrix and the absorbent, complete separation between the absorbed fluid phase and the captured and collected solid phase on the porous matrix is ensured.

A number of separator layers have been evaluated and it has been found that the same may be composed of a glass fiber layer (Whatman), blotter paper (Gillman), or a porous plastic layer (Porex or Pellon) with essentially the same results. Likewise, a considerable number of capture matrices have been evaluated and found to be suitable. Glass fiber filters (Whatman GF/A), regenerated cellulosic membranes (Schleicher and Schuell) and microporous membranes (Millipore MF series membranes HAWP, SSWP, SMWP and SCWP with pore sizes of 0.45, 3, 5 and 8 microns respectively) have all been successfully utilized for capturing and collecting solid phase, metal-containing composites, in accordance with the present invention. It has not yet been determined which of these capture matrices might be the best in commercial application and it could be that one matrix might be better for one situation and another matrix for another situation. However, in the laboratory, the glass fiber filter has been found to be particularly useful.

In selecting an appropriate capture matrix, two factors, porosity and nonspecific binding properties, must be considered. Larger pore size or porosity will allow for more rapid flow and thus may be favored, especially in those cases where external pressure or vacuum cannot be applied. However, if the capture matrix is too porous or open, the solid phase, metal-containing composite might pass through the matrix and thus not be visible. It has also been observed that some capture matrices will bind antibody coated metal particles nonspecifically, i.e., in the absence of an immune reaction, and perhaps even in the absence of solid phase capture particles. Such nonspecific binding is well known to those skilled in the art and may be suppressed by pretreating the capture matrices with nonspecific binding blockers such as polyvinylpyrrolidone (PVP), Calf serum, bovine serum albumin and/or a variety of other materials and polymers which are widely known in the relevant art. One format which might be successfully employed in accordance with the present invention is disclosed in U.S. Pat. No. 4,632,901, the principal difference being that the membrane to be utilized in accordance with the present invention does not have an immunoreagent bound thereto. Rather, the membrane for the present invention simply is used as a mechanical filter. Other prior art devices which might be adapted for the purposes of the present invention are disclosed in U.S. Pat. Nos. 4,246,339 and 4,407,943. Again, these prior art devices have a reactant bound to the membrane whereas in the present invention there is no necessity for a reactant to be bound to the membrane. Rather, the composite is simply collected by a filtration type procedure.

In accordance with the present invention, although the antibody coated solid particles and the antibody coated metal particles are each multivalent since each particle carries a multiplicity of antibodies, it has been determined that the final dispersed, collectible, solid phase, metal-containing composite produced as a result of the assay simply comprises the solid phase particles coated with gold particles bound thereto. The coated gold particles attached to a solid phase particle as a result of the immunological reaction of the invention do not appear to link with another antibody coated solid phase particle even though each gold particle carries unreacted antibody on its surface. The reason for this is not fully understood; however, it has been determined that such linking does not occur and that the present invention does not involve an agglutination or agglomeration phenomena such as is exploited in accordance with U.S. Pat. No. 4,313,734.

Through the use of the present invention, and in particular through the use of water suspensible particles such as latex, glass beads, etc., and antibody coated gold sol particles, an assay for hCG in accordance with the present invention is capable of detecting as little as 37.5 mIU of hCG, and the ultimate level of sensitivity has not yet been established. It is felt that the improved results obtained as a result of the present invention arise from the use of suspensible particles offering considerable more surface area, and the capturing of the particles in a limited volume, thereby multiplying several fold the color to be perceived by the human eye.

It should also be noted that in prior art assays which employ agglutination principles, the color change in the liquid phase, usually from red to a purplish blue, is used to measure the course of the reaction. Thus, one schooled in the art would anticipate, that when antibody coated gold sols and antibody coated beads are mixed, the same would co-agglutinate to produce a red to purplish to blue color transition in the liquid phase. As it so happens, in the case of the present invention no such color transition occurs, either in the liquid phase or in the solid phase, and the latter, when collected, and particularly when gold has been employed as a marker, possesses an intense red coloration which is readily visible to the human eye.

Although the present invention is not limited to detection and or determination of analytes in human urine, in commercial application, and particularly where pregnancy and ovulation tests are involved, the test solution will generally comprise a sample of first morning urine. Urine has been found to contain a number of nonspecific, dispersed, particulate contaminants and/or impurities which may provide false positive results and otherwise interfere with the test of the present invention. Accordingly, in conducting the test of the invention using urine samples it has generally been found to be desirable to filter urine samples to remove such contaminants before conducting the test procedures. Any sort of filter which is capable of removing the particulate contaminants may be used; however, high density porous polyethylene Porex plugs of the sort described above for use as the separator have been found to be highly effective for such filtering purposes.

We claim:

1. In a process for the determination and detection of an immunologically reactive analyte in an aqueous sample, the steps of:
   (a) providing a labelled component comprising the coupling product of a first immunologically reactive substance and a metal-containing particle of a size and character to facilitate the maintenance of a stable, monodispersed suspension of the labelled component;
   (b) providing a solid phase component comprising the coupling product of a second immunologically reactive substance and a solid phase particle of a size and character to facilitate the maintenance of a stable suspension of the solid phase component and subsequent collection of a composite formed therefrom;
   (c) forming a mixed aqueous suspension of said components and which contains a sample to be analyzed for the analyte, said first and second substances being different and capable of binding directly or indirectly as a function of the presence of said analyte to thereby form a collectible, solid phase, metal-containing composite;
   (d) allowing the substances to bind to form said composite;
   (e) collecting the composite; and
   (f) determining or detecting the analyte in the sample by evaluating, through direct visual examination, the presence of metal in the collected solid phase composite.

2. The process of claim 1, wherein said analyte is a biologically active substance selected from the group consisting of ligands and anti-ligands.

3. The process of claim 1, wherein said metal-containing particles are metal sol particles.

4. The process of claim 3, wherein said metal sol particles have a particle size in the range of from about 50 Angstroms to about 1000 Angstroms.

5. The process of claim 4, wherein said metal sol particles have a particle size in the range of from about 135 to about 500 Angstroms.

6. The process of claim 3, wherein said particles are gold sol particles.

7. The process of claim 4, wherein said particles are gold sol particles.

8. The process of claim 5, wherein said particles are gold sol particles.

9. The process of claim 1, wherein said labelled component is prepared by coupling the first substance directly to the metal-containing particle.

10. The process of claim 1, wherein ,said labelled component is prepared by coupling the first substance to the particle using a biotin avidin linkage.

11. The process of claim 10, wherein said labelled component is prepared by biotinylating the first substance, coating the metal containing particle with an avidin compound and reacting the biotin on the first substance with the avidin compound on the particle.

12. The process of claim 1, wherein said labelled component is prepared by coupling the first substance to the particle using bovine serum albumin.

13. The process of claim 1, wherein said solid phase component is prepared by coupling the second substance directly to the solid phase particle.

14. The process of claim 1, wherein said solid phase component is prepared by coupling the second substance to the particle using a bovine serum albumin linkage.

15. The process of claim 1, wherein said solid phase component is prepared by coupling the second substance to the particle using gelatin.

16. The process of claim 11, wherein the labelled component is formed by adding the avidin coated metal-containing particle to the aqueous suspension after all of the other ingredients of the mixed aqueous suspension have been mixed together.

17. The process of claim 1, wherein said first and second substances are each capable of binding a respective different site of the analyte to form a sandwich.

18. The process of claim 17, wherein said first and second substances are each antibodies and the analyte is an antigen.

19. The process of claim 1, wherein said first and second substances bind each other.

20. The process of claim 19, wherein one of said substances in an antibody and the other is an antigen.

21. The process of claim 19, wherein the first substance of the labelled component is an antibody.

22. A process as set forth in claim 1, wherein said collecting comprises capturing the composite on the surface of a porous filtration element which permits passage of the filtrate but prevents passage of the composite.

23. A process as set forth in claim 1, wherein said collecting comprises causing the composite to gravitate into a limited volumetric space by sedimentation to thereby form a concentrated pellet.

24. A process as set forth in claim 1, wherein said collecting comprises subjecting the aqueous suspension to centrifugation to force the composite into a limited volumetric space to thereby form therefrom a densely packed pellet.

25. The process of claim 22, wherein the filtrate is pulled through the element by centrifugal force.

26. The process of claim 22, wherein the filtrate is pulled through the element by capillary force.

27. A kit of materials for use in determining and detecting an immunologically reactive analyte in an aqueous sample comprising:
   a labelled component comprising the coupling product of a first immunologically reactive substance and a metal-containing particle of a size and character to facilitate the maintenance of a stable, monodisperse suspension of the labelled component;
   a solid phase component comprising the coupling product of a second immunologically reactive substance and a solid phase particle of a size and character to facilitate the maintenance of a stable suspension of the solid phase component and subsequent collection of a composite formed therefrom,
   said components being operable and cooperable to permit formation therefrom of a mixed aqueous suspension of said components and which contains a sample to be analyzed for the analyte, the first substance of said labelled component and the second substance of said solid phase component being different and capable of binding directly or indirectly as a function of the presence of said analyte to thereby form a dispersed, collectible, solid phase, metal-containing composite; and collector means for collecting and directly visually examining the composite to evaluate the presence of metal bound in the collected solid phase composite and thereby detect or determine the presence of analyte in the sample.

28. A kit as set forth in claim 27, wherein said first and second substances are each capable of binding a respective different site of the analyte to form a sandwich.

29. A kit as set forth in claim 28, wherein said first and second substances are each antibodies and the analyte is an antigen.

30. A kit as set forth in claim 27, wherein said first and second substances bind each other.

31. A kit as set forth in claim 27, wherein said metal-containing particles are metal sol particles.

32. A kit as set forth in claim 31, wherein said metal sol particles have a particle size in the range of from about 50 to about 1000 Angstroms.

33. A kit as set forth in claim 32, wherein said metal sol particles have a particle size in the range of from about 135 to about 500 Angstroms.

34. A kit as set forth in claim 31, wherein said particles are gold sol particles.

35. A kit as set forth in claim 32, wherein said particles are gold sol particles.

36. A kit as set forth in claim 33, wherein said particles are gold sol particles.

37. A stable, collected mass of a solid phase metal-containing composite capable of being directly visually observed to indicate the initial presence, absence or amount of an analyte in an aqueous sample, said composite comprising:
   a labelled component comprising the coupling product of a first immunologically reactive substance and a metal-containing particle of a size and character to initially facilitate the maintenance of a stable, monodispersed suspension of the labelled component; and
   a solid phase component comprising the coupling product of a second immunologically reactive substance and a solid phase particle of a size and character to initially facilitate the maintenance of a stable suspension of the solid phase component and subsequent collection of said composite,
   said substances being different and directly or indirectly bound to each other to present said composite.

38. The collected mass of claim 37, wherein said composite includes the analyte and said first and second substances are each bound to a respective different site of the analyte in sandwich form.

39. The composite of claim 38, wherein said mass is collected on porous filter element.

40. The composite of claim 38, wherein said mass is collected at the bottom of a test tube.

41. The collected mass of claim 37, wherein said first and second substances are bound directly to each other.

* * * * *

UNITED STATES PATENT AND TRADEMARK OFFICE
CERTIFICATE OF CORRECTION

PATENT NO. : 4,859,612

DATED : August 22, 1989

INVENTOR(S) : FRANCIS X. COLE et al.

It is certified that error appears in the above-identified patent and that said Letters Patent is hereby corrected as shown below:

```
Column 1,  line 52, insert "." after --antibodies--.
Column 3,  line 42, insert "." after --observed--;
           line 45, change "sole" to --some--.
Column 8,  line 16, after "above" insert --.--.
Column 10, line 45, change "C." to --C--.
Column 11, line 63, "hydrc" should be --hydro--.
Column 13, line 23, delete "the";
           line 24, after "hour" insert --,--;
           line 29, "anahdride" should be --anhydride--;
           line 36, "C.," should be --C,--.
Column 15, line 31, change "3" to --35--.
Column 16, line 34, "u" should be --ul--.
Column 17, line 8, "metal containing" should be
                   --metal-containing--.
Column 19, line 55, ", said" should be --said--;
           line 60, "metal containing" should be
                   --metal-containing--.
```

UNITED STATES PATENT AND TRADEMARK OFFICE
CERTIFICATE OF CORRECTION

PATENT NO. : 4,859,612

DATED : August 22, 1989

INVENTOR(S) : FRANCIS X. COLE et al.

It is certified that error appears in the above-identified patent and that said Letters Patent is hereby corrected as shown below:

Column 20, line 24, delete "of the labelled component".

Signed and Sealed this

Third Day of April, 1990

Attest:

*Attesting Officer*

HARRY F. MANBECK, JR.

*Commissioner of Patents and Trademarks*